＃

US007396927B2

(12) United States Patent
Niddam-Hildesheim et al.

(10) Patent No.: US 7,396,927 B2
(45) Date of Patent: Jul. 8, 2008

(54) PROCESS FOR PREPARATION OF ROSUVASTATIN CALCIUM

(75) Inventors: Valerie Niddam-Hildesheim, Ein Vered (IL); Greta Sterimbaum, Rishon-Lezion (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/925,430

(22) Filed: Aug. 24, 2004

(65) Prior Publication Data

US 2005/0080134 A1 Apr. 14, 2005

Related U.S. Application Data

(60) Provisional application No. 60/534,678, filed on Jan. 6, 2004, provisional application No. 60/498,764, filed on Aug. 28, 2003.

(51) Int. Cl.
C07D 239/42 (2006.01)
A61K 31/505 (2006.01)
A61P 3/06 (2006.01)

(52) U.S. Cl. .............. 544/297; 544/332; 544/330

(58) Field of Classification Search ............ 544/332, 544/316, 318, 297, 330; 548/491, 537; 549/292
See application file for complete search history.

(56) References Cited

U.S. PATENT DOCUMENTS

| 4,231,938 | A | 11/1980 | Monaghan et al. |
| 4,346,227 | A | 8/1982 | Terahara et al. |
| 4,444,784 | A | 4/1984 | Hoffman et al. |
| 4,739,073 | A | 4/1988 | Kathawala |
| 5,006,530 | A | 4/1991 | Angerbauer et al. |
| 5,177,080 | A | 1/1993 | Angerbauer et al. |
| 5,260,440 | A * | 11/1993 | Hirai et al. ............ 544/332 |
| 5,354,879 | A | 10/1994 | Konoike et al. |
| RE37,314 | E | 8/2001 | Hirai et al. |
| 6,316,460 | B1 | 11/2001 | Creekmore et al. |
| 6,333,198 | B1 | 12/2001 | Edmeades et al. |
| 6,777,552 | B2 * | 8/2004 | Niddam-Hildesheim et al. ............ 544/332 |
| 6,858,618 | B2 | 2/2005 | Raza et al. |
| 2005/0131066 | A1 | 6/2005 | Niddam-Hildesheim et al. |
| 2005/0222415 | A1 | 10/2005 | Kumar et al. |
| 2006/0116391 | A1 * | 6/2006 | Horbury et al. ............ 514/275 |

FOREIGN PATENT DOCUMENTS

| EP | 0 850 902 | 7/1998 |
| EP | 0 521 471 | 10/2000 |
| WO | WO 00/17150 | 3/2000 |
| WO | WO 00/49014 A | 8/2000 |
| WO | WO 01/60804 | 8/2001 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 A1 * | 2/2004 |
| WO | WO 2004/052867 | 6/2004 |
| WO | WO 2005/021511 | 3/2005 |
| WO | WO 2006/035277 | 4/2006 |
| WO | WO 2006/079611 | 8/2006 |
| WO | WO 2006 100689 | 9/2006 |
| WO | WO 2006/106526 | 10/2006 |
| WO | WO 2006/136407 | 12/2006 |
| WO | WO 2006/136408 | 12/2006 |
| WO | WO 2007/007119 | 1/2007 |

OTHER PUBLICATIONS

Watanabe et al. Synthesis and Biological Activity of Methanesulfonamide Pyrimidine- and N-methanesulfonyl Pyrrole-Substituted 3,5-Dihydroxy-6-heptenoates, a Novel Series of HMG-CoA Reductase Inhibitors. Bioorg Med Chem. Feb. 1997;5(2):437-44.*

Anelli, et al., "Fast And Selective Oxidation Of Primary Alcohols To Aldehydes Or To Carboxylic Acids And Of Secondary Alcohols To Ketones Mediated By Oxoammonium Salts Under Two-Phase Conditions", *J. Org. Chem.*, 1987, pp. 2559-2562, vol. 52, No. 12.

Hull, et al., "Quantification Of Rosuvastatin In Human Plasma By Automated Solid-Phase Extraction Using Tandem Mass Spectrometric Detection", *Journal of Chromatography B: Biomedical Sciences & Applications*, 2002, pp. 219-228, vol. 772, No. 2.

Konoike, et al. "Practical Synthesis of Chiral Synthons for the Preparation of HMG-CoA Reductase Inhibitors" J. Org. Chem., vol. 59, 1994, pp. 7849-7854.

Lenz, et al., "Tetra-*N*-Propylammonium Perruthenate (TPAP)-Catalysed Oxidations Of Alcohols Using Molecular Oxygen As A Co-Oxidant", *J. Chem. Soc., Perkin Trans. 1*, 1997, 3291-3292.

Ley, et al., *Synthesis*, 1994, 639-666.

Lipid Research Clinics Program, "The Lipid Research Clinics Coronary Primary Prevention Trial Results: I. Reduction In Incidence Of Coronary Heart Disease", *J.A.M.A.*, 1984, 351-74, vol. 251, No. 3.

*Shionogi Annual Report*, 1996, Direct Communications, Shionogi, Feb. 8, 1999 & Feb. 25, 2000.

Scandinavian Simvastatin Survival Study Group, "Randomised Trial Of Cholesterol Lowering In 4444 Patients With Coronary Heart Disease: The Scandinavian Survival Study (4s)", *The Lancet*, 1994, pp. 1383-1389, vol. 344.

Snyder, et al., *Introduction To Modern Liquid Chromatography*, 2nd ed., John Wiley & Sons: New York, 1979, pp. 549, 552, 571-572.

Strobel, et al., *Chemical Instrumentation: A Systematic Approach*, 3rd ed., Wiley & Sons: New York, 1989, pp. 391-393, 879, 894, 922, 924-925, 953.

Witztum, "Chapter 36: Drugs Used In The Treatment Of Hyperlipoproteinemias", *Goodman & Gilman's The Pharmacological Basis Of Therapeutics*, 9th ed., pp. 875-897.

* cited by examiner

*Primary Examiner*—Venkataraman Balasubram
(74) *Attorney, Agent, or Firm*—Kenyon & Kenyon LLP

(57) ABSTRACT

The present invention provides processes for preparing calcium salts of statin, particularly rosuvastatin calcium salt substantially free of impurities on an industrial scale.

38 Claims, 1 Drawing Sheet

Figure 1: HPLC analysis corresponding to example 1

| Sample | RRT 0.58 | RRT 0.62 | RRT 0.90 | RRT 1.0 | RRT 1.18 | RRT 1.22 | RRT 1.31 | RRT 1.41 | RRT 1.56 | RRT 1.60 | RRT 2.68 | RRT 3.66 | RRT 3.89 | RRT 3.93 | RRT 3.99 | RRT 4.10 |
|---|---|---|---|---|---|---|---|---|---|---|---|---|---|---|---|---|
| End of reaction Reaction mixture | | 0.11 | 0.37 | 98.04 | 0.09 | 0.05 | 0.14 | 0.12 | 0.03 | 0.02 | | 1.03 | | 0.08 | 0.24 | |
| After evaporation EtOH/H$_2$O | | 0.11 | 0.02 | 98.03 | 0.09 | 0.06 | 0.07 | 0.06 | 0.08 | 0.02 | 0.03 | 1.07 | | 0.07 | 0.18 | 0.03 |
| EtOAc phase after extraction | 13.48 | | | 36.60 | 2.92 | | | | | | | 30.45 | | 9.54 | 4.83 | |
| Aqueous phase after extraction | 0.02 | 0.11 | 0.04 | 98.34 | 0.06 | 0.09 | 0.08 | | 0.07 | | | 1.17 | | | | |
| ML after formation Ca salt | 0.75 | | | 99.25 | | | | | | | | | | 3.62 | | 0.49 |
| Rosuvastatin Calcium solid | 0.09 | | 0.04 | 99.63 | | 0.05 | 0.04 | 0.05 | 0.07 | | | | | | | |

PROCESS FOR PREPARATION OF ROSUVASTATIN CALCIUM

CROSS-REFERENCE TO RELATED APPLICATIONS

This application claims the benefit of U.S. Provisional Application Nos. 60/498,764 filed on Aug. 28, 2003 and 60/534,678 filed on Jan. 6, 2004, the disclosures of which are incorporated by reference in their entirety herein.

FIELD OF THE INVENTION

The present invention relates to processes for preparation of rosuvastatin calcium.

BACKGROUND OF THE INVENTION

The class of drugs called statins are currently the most therapeutically effective drugs available for reducing low-density lipoprotein (LDL) particle concentration in the blood stream of patients at risk for cardiovascular disease and thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis. Goodman and Gilman, The Pharmacological Basis of Therapeutics, page 879 (9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease. J.A.M.A. 1984, 251, 351-74.

Currently available statins include lovastatin, simvastatin, pravastatin, fluvastatin, cerivastatin and atorvastatin. Lovastatin (disclosed in U.S. Pat. No. 4,231,938) and simvastatin (disclosed in U.S. Pat. No. 4,444,784) are administered in the lactone form. After absorption, the lactone ring is opened in the liver by chemical or enzymatic hydrolysis, and the active hydroxy acid is generated. Pravastatin (disclosed in U.S. Pat. No. 4,346,227) is administered as the sodium salt. Fluvastatin (disclosed in U.S. Pat. No. 4,739,073) and cerivastatin (disclosed in U.S. Pat. No. 5,006,530 and 5,177,080), also administered as the sodium salt, are entirely synthetic compounds that are in part structurally distinct from the fungal derivatives of this class that contain a hexahydronaphthalene ring. Atorvastatin and two new "superstatins," rosuvastatin and pitavastatin, are administered as calcium salts.

Rosuvastatin calcium (7-[4-(4-fluorophenyl)-6-isopropyl-2-(N-methyl-N-methylsulfonylamino) pyrimidin-5-yl]-(3R, 5S)-dihydroxy-(E)-6-heptenoic acid) is an HMG-CoA reductase inhibitor, developed by shionogi for the once daily oral treatment of hyperlipidaemia (Ann Rep, Shionogi, 1996; Direct communications, Shionogi, 8 Feb. 1999 & 25 Feb. 2000). It is a superstatin, which can lower LDL-cholesterol and triglycerides more effectively than first generation drugs. Rosuvastatin calcium has the following chemical formula:

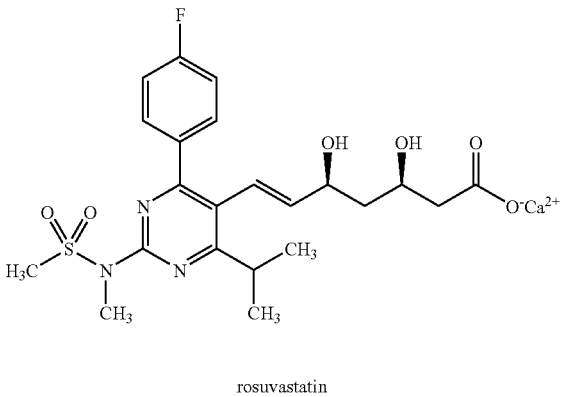

rosuvastatin

Rosuvastatin calcium is marketed under the name CRESTOR for treatment of a mammal such as a human. According to the maker of CRESTOR, it is administered in a daily dose of from about 5mg to about 40 mg. For patients requiring less aggressive LDL-C reductions or who have pre-disposing factors for myopathy, the 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses. WO 03/032995 further discloses a method of preventing dementia by administering to a patient rosuvastatin.

U.S. Pat. No. 5,260,440 discloses the process to produce rosuvastatin salt. The process of U.S. Pat. No. 5,260,440 starts with the methyl ester of rosuvastatin, known an (methyl-7-[4-(4-fluorophenyl)-6-isopropyl-2-(N-methyl-N-methylsulfonylamino) pyrimidin-5-yl]-(3R,5S)-dihydroxy-(E)-6-heptenate (methyl rosuvastatin)). The process for preparation of the intermediates disclosed in the '440 patent is incorporated herein by reference.

In the '440 patent, rosuvastatin sodium is prepared from its methyl ester according to Example 1 (6) by adding sodium hydroxide to a solution of the methyl ester in ethanol, followed inter alia by distillation, followed by addition of ether to the residue obtained from distillation. When preparing a salt of rosuvastatin, the present applicants found that diethyl ether may not be used in production; after distillation of the solvent, the present applicants obtained a viscous oil that hardly precipitates in diethyl ether.

Preparation of rosuvastatin calcium is also disclosed in WO 04/052867, WO 04/014872, WO 00/49041 and WO 03/097614. The processes disclosed in these publications for preparation of rosuvastatin calcium are of general nature.

There is a need in the art for processes that allow for preparation of highly pure rosuvastatin calcium in a facile manner on an industrial scale.

SUMMARY OF THE INVENTION

The invention encompasses processes for producing rosuvastatin calcium comprising: (a) reacting a $C_1$ to $C_4$ alkyl ester of rosuvastatin with a base in the presence of a $C_1$ to $C_4$ alcohol to obtain a solution; (b) concentrating the solution to obtain a residue; (c) combining the residue with water to obtain an aqueous solution; (d) washing the aqueous solution with a water immiscible organic solvent; (e) removing traces of the organic solvent; (f) adding a source of calcium to the solution to precipitate rosuvastatin calcium; and (g) recovering the rosuvastatin calcium salt. The ester may be a methyl ester or a t-butyl ester. The base of step (a) may be selected from the group consisting of sodium hydroxide, potassium hydroxide, and barium hydroxide. The process may further comprise stirring the solution of step (a) before proceeding to step (b). The concentrating step (b) may be performed by evaporation, and optionally under reduced pressure. Step (a) may be carried out by adding the base to a suspension of the ester in the alcohol, wherein the alcohol may be ethanol. The organic solvent of the process may be a $C_4$ to $C_7$ ester or ketone, such as ethylacetate. Removing traces of the organic solvent in step (e) may be carried out by evaporation. In one particular embodiment, the evaporation is carried out under reduced pressure. The source of calcium in step (f) may be calcium chloride. The recovering step may be carried out by filtration.

Another embodiment of the invention encompasses processes for producing rosuvastatin calcium salt comprising: combining a suspension of t-butyl ester of rosuvastatin in ethanol with sodium hydroxide to obtain a solution, and stirring during or after the combining; evaporating the solution under reduced pressure to obtain a residue; combining the residue with water to obtain an aqueous solution; washing the aqueous solution with ethyl acetate; evaporating traces of the ethyl acetate under reduced pressure; adding calcium chloride to the solution to precipitate rosuvastatin calcium; and filtering the rosuvastatin calcium salt.

Yet another embodiment of the invention encompasses processes for producing rosuvastatin calcium salt comprising: reacting a $C_1$ to $C_4$ alkyl ester of rosuvastatin in a water immiscible phase, with a base in an aqueous phase, in the presence of a phase transfer catalyst to obtain rosuvastatin in the aqueous phase; adding a source of calcium to the aqueous phase to precipitate rosuvastatin calcium; and recovering the rosuvastatin calcium salt. The ester may be a t-butyl ester. The process may further comprise a step of removing traces of the water immiscible solvent before adding the source of calcium and/or stirring during the reaction. The water immiscible phase may be a solvent selected from the group consisting of substituted and unsubstituted $C_5$ to $C_{12}$ hydrocarbon, $C_4$ to $C_7$ ester, $C_4$ to $C_7$ ketone, and mixtures thereof. In one particular embodiment, the hydrocarbon is toluene or chlorobenzene. The phase transfer catalyst of the reaction may be an alkyl, aryl, alkaryl, or arylalkyl ammonium salt.

Another embodiment of the invention encompasses processes for producing rosuvastatin calcium salt comprising: reacting, t-butyl ester of rosuvastatin with sodium hydroxide in presence of water, a tetrabutylammonium phase transfer catalyst and an organic solvent selected from the group consisting of toluene and chlorobenzene to obtain rosuvastatin in the water; removing traces of the toluene or chlorobenzene from the water; adding calcium chloride to the water to precipitate rosuvastatin calcium; and filtering the rosuvastatin calcium salt. The process may further comprise stirring during the reaction.

Yet another embodiment of the invention encompasses processes for producing rosuvastatin calcium salt substantially free of impurities comprising the steps of: reacting a $C_1$ to $C_4$ ester of rosuvastatin with a base in a two phase system of water and acetonitrile; concentrating the water phase to obtain a residue; adding a source of calcium and water to the residue to form a solution in water; and recovering rosuvastatin calcium as a precipitate. The process may further comprising stirring during the reaction. In the process, the impurities may be equal or less than about 0.3% as measured by area percentage HPLC.

In the processes of the invention, the calcium salt may contain less than or about 0.4% total impurities as measured by area percentage HPLC. In the processes of the invention, the rosuvastatin calcium salt does not have detectable levels of impurities when measured by HPLC at RRT 0.62, 1.18, 1.26, 1.60, 2.68, 3.66, 3.89, 3.93,or 4.10. In a particular embodiment, the impurities are less than about 0.01% as measured by HPLC area percentage.

Another embodiment of the invention encompasses processes for producing rosuvastatin calcium comprising: (a) preparing a solution of rosuvastatin sodium; (b) concentrating the solution to obtain a residue; c) combining the residue with water to obtain an aqueous solution; d) washing the aqueous solution with a water immiscible organic solvent; e) removing traces of the organic solvent; (f) adding a source of calcium to the solution to precipitate rosuvastatin calcium; and (g) recovering the rosuvastatin calcium salt.

Yet another embodiment of the invention encompasses rosuvastatin calcium in solid state having less than or of about 0.4% total impurities as measured by area percentage HPLC. In a particular embodiment, the rosuvastatin calcium may have impurities equal or less than about 0.3% as measured by area percentage HPLC. Another particular embodiment encompasses rosuvastatin calcium in a solid state, wherein the calcium salt does not have detectable level of impurities at RRT 1.26 when measured by HPLC. The rosuvastatin calcium salt may not have further detectable level of impurities when measured by HPLC at RRT 0.62, 1.18, 1.60, 2.68, 3.66, 3.89, 3.93,or 4.10. For example, the impurities of the rosuvastatin calcium are less than about 0.01% as measured by HPLC area percentage.

Another embodiment of the invention encompasses pharmaceutical formulations for administration to a mammal in need of a reduction in blood cholesterol level comprising rosuvastatin calcium as active ingredient, and at least a pharmaceutically acceptable excipient.

Yet another embodiment of the invention encompasses methods of treating a mammal in need of a reduction in blood cholesterol level comprising the step of administering the pharmaceutical formulation having rosuvastatin calcium as the active ingredient to the mammal in need thereof.

BRIEF DESCRIPTION OF THE FIGURES

FIG. 1 summarizes the purity at various points in the process of example 1 as determined by high pressure liquid chromatography ("HPLC").

DETAILED DESCRIPTION OF THE INVENTION

The present invention relates to a process of preparing rosuvastatin calcium salt substantially free of impurities.

Unless otherwise specified, the term "ambient temperature" refers to a temperature of from about 5° C. to about 25° C. Most preferably, "ambient temperature" refers to a temperature of about 25° C. The term "reduced pressure" generally refers to a pressure of about 10 mmHg to about 50 mmHg.

The present invention provides for a process for preparing rosuvastatin from a $C_1$ to $C_4$ alkyl ester of rosuvastatin, most preferably t-butyl ester of rosuvastatin. In one embodiment, the t-butyl ester of rosuvastatin is reacted with at least about 1 equivalent of a base, in the presence of a $C_1$ to $C_4$ alcohol, and stirred at ambient temperature, followed by precipitation from water. A preferred alcohol is ethanol. The reaction may be carried out by suspending the ester in the alcohol, followed by addition of the base to obtain a solution of the salt.

The base is preferably added portionwise, with preferred bases being alkali and alkaline earth metal bases, other than calcium hydroxide, such as sodium hydroxide, potassium hydroxide and barium hydroxide. Sodium hydroxide is particularly preferred for use as a base.

During or after the combining of the base with the ester, the resulting solution is preferably stirred for at least about 5 minutes, more preferably for about 1 hour. The solution is then preferably filtered in order to remove any impurities originating from the starting material.

The process of the present invention may also be carried out by starting with a solution of rosuvastatin salt in a solvent, such as the sodium salt in a $C_1$ to $C_4$ alcohol, rather than starting from the ester. Such solution may for example be prepared by starting with rosuvastatin sodium as a solid, and adding the solid to an alcohol.

The reaction mixture is then preferably concentrated to obtain a residue. The term residue refers to an oil containing rosuvastatin salt, resulting from removal of solvent from a solution of the rosuvastatin salt. The removal of solvent is preferably carried out by evaporation under reduced pressure (below about 50 mmHg) and at a temperature of about 40° C. to about 70° C., with about 60° C. being preferred.

The residue is then distributed between an aqueous and an organic water immiscible phase, wherein the salt of rosuvastatin moves into the aqueous phase and the impurities into the organic phase. The distribution may be carried out by washing the solution of the salt in the aqueous solvent with the organic solvent. The aqueous phase preferably contains water, but may also contain other solvents in a mixture with water, as long as the other solvents allow for a two phase system and solubility of the salt in at least the aqueous phase.

In a preferred embodiment, the residue is combined with water to obtain a solution, and then the rosuvastatin salt in the solution is washed with an organic solvent. Preferably, water is added in the amount of at least about 1:1 or 1:0.5 water: lower alcohol (v/v) used in the previous steps.

Preferably the organic solvent is a $C_4$ to $C_7$ ester or ketone such as ethyl acetate or methyl ethyl ketone. Other organic solvents include alkyl carbonates such as di-ethyl carbonate, $C_5$ to $C_{12}$ aromatic and saturated hydrocarbons such as toluene, benzene, xylene, cyclic and acyclic hexane and heptane.

After the washing step with the organic solvent, traces of organic solvent remaining may be removed by conventional techniques in the art, such as evaporation under reduced pressure at a temperature of about 5° C. to about 80° C. more preferably about 60° C.

The salt may be converted to a calcium salt by combining the solution with a source of calcium such as $CaCl_2$, preferably at ambient temperature. After combining, the reaction mixture is preferably stirred, and the rosuvastatin calcium salt is recovered by conventional techniques such as filtration, and preferably washed.

In another embodiment, a two phase system is used with a phase transfer catalyst. Examples of phase transfer catalysts include quaternary ammonium salts, such as a bromide or sulfate salt of tetrabutylammonium, hexadecyltrimethylammonium and benzyltriethylammonium. A crown ether or a quaternary phosphonium salt may also be used as a phase transfer catalyst.

In this embodiment, an aqueous phase and a water immiscible phase is used. A water immiscible organic solvent is used in which the ester of rosuvastatin or other desired rosuvastatin derivative is substantially soluble. Examples of such organic solvents include saturated and aromatic, substituted and unsubstituted $C_5$ to $C_{12}$ hydrocarbons, and $C_4$ to $C_7$ ketones and esters. Specific examples of such solvents include benzene, toluene, chlorobenzene, ethyl acetate, methyl ethyl ketone, and cyclic and acyclic hexane and heptane. The aqueous phase contains a base, as described above, which through the use of the phase transfer catalyst is taken to the water immiscible phase, resulting in rosuvastatin. Rosuvastatin then moves to the aqueous phase. Rosuvastatin calcium is recovered from the aqueous phase as described above.

In another embodiment, rosuvastatin calcium is prepared from an ester derivative of rosuvastatin with a two phase system in the absence of a phase transfer catalyst. In this embodiment, a preferred two phase system is water and acetonitrile, under basic conditions so that the two solvents are not substantially miscible. Alkali metal or alkaline earth metals may be used as bases. In one embodiment, use of sodium hydroxide results in the sodium salt, which may then be recovered from both the organic and aqueous phase as illustrated in example 7. The organic and the aqueous phase may be concentrated, and water and a source of calcium added to precipitate the rosuvastatin calcium from solution in water.

The present invention also relates to rosuvastatin calcium salt substantially free of impurities, i.e., the calcium salt contains less than about 0.5% impurities as an area percentage by HPLC, more preferably less than or of 0.4% total impurities, and most preferably less than or of about 0.3% total impurities. In one embodiment, the calcium salt does not have detectable impurities level when measured by HPLC at RRT 0.62, 1.18, 1.60, 2.68, 3.66, 3.89, 3.93 and 4. 10. The detection level of the HPLC used in the present invention is about 0.01% area percentage. The RRT values expressed herein are specific to the HPLC conditions disclosed herein.

Relative to CRESTOR, the rosuvastatin calcium of the present invention has a higher purity profile and does not have a detectable level of an impurity at RRT 1.26, which is present in CRESTOR. Based in analysis by LC-MS, this impurity has a molecular weight of 479.

Pharmaceutical formulations/compositions of the present invention contain rosuvastatin calcium substantially free of impurities. The rosuvastatin calcium prepared by the processes of the present invention is ideal for pharmaceutical formulation. In addition to the active ingredient(s), the pharmaceutical formulations of the present invention may contain one or more excipients. Excipients are added to the formulation for a variety of purposes.

Diluents increase the bulk of a solid pharmaceutical formulation, and may make a pharmaceutical dosage form containing the formulation easier for the patient and care giver to handle. Diluents for solid formulations include, for example, microcrystalline cellulose (e.g. Avicel® and beta form), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical formulations that are compacted into a dosage form, such as a tablet, may include excipients whose functions include helping to bind the active ingredient and other excipients together after compression. Binders for solid pharmaceutical formulations include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl-cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical formulation in the patient's stomach may be increased by the addition of a disintegrant to the formulation. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid formulation and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered formulation, the formulation is subjected to pressure from a punch and dye. Some excipients and active ingredients have a tendency to adhere to the surfaces of the punch and dye, which can cause the product to have pitting and other surface irregularities. A lubricant can be added to the formulation to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the formulation of the present invention include maltol, vanillin, ethyl vanillin, menthol, citric acid, fumaric acid, ethyl maltol and tartaric acid.

Solid and liquid formulations may also be dyed using any pharmaceutically acceptable colorant to improve their appearance and/or facilitate patient identification of the product and unit dosage level.

In liquid pharmaceutical formulations of the present invention, valsartan and any other solid excipients are dissolved or suspended in a liquid carrier such as water, vegetable oil, alcohol, polyethylene glycol, propylene glycol or glycerin.

Liquid pharmaceutical formulations may contain emulsifying agents to disperse uniformly throughout the formulation an active ingredient or other excipient that is not soluble in the liquid carrier. Emulsifying agents that may be useful in liquid formulations of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical formulations of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid formulation may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid formulations of the present invention include powders, granulates, aggregates and compacted formulations. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the formulation, preferably a powdered or granulated solid formulation of the invention, within either a hard or soft shell. The shell may be made from gelatin and optionally contain a plasticizer such as glycerin and sorbitol, and an opacifying agent or colorant.

The active ingredient and excipients may be formulated into formulations and dosage forms according to methods known in the art.

A formulation for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tabletted, or other excipients may be added prior to tableting, such as a glidant and/or a lubricant.

A tableting formulation may be prepared conventionally by dry blending. For example, the blended formulation of the actives and excipients may be compacted into a slug or a sheet and then comminuted into compacted granules. The compacted granules may subsequently be compressed into a tablet.

As an alternative to dry granulation, a blended formulation may be compressed directly into a compacted dosage form using direct compression techniques. Direct compression produces a more uniform tablet without granules. Excipients that are particularly well suited for direct compression tableting include microcrystalline cellulose, spray dried lactose, di-calcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid formulations of the present invention include powders, granulates, aggregates and compacted formulations. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

In addition to excipients, the pharmaceutical formulations of the present invention may contain an adjuvant.

EXAMPLES

The Impurity Profile Determination of Rosuvastatin Ca comprised testing a sample using HPLC. Typically, the HPLC testing parameters included a column of Hypersil BDS C18 5 μm 4.6*250 mm (Part No. 28105-020 or equivalent column) at a temperature of 25° C. and eluted with a two solvent system. A first reservoir, Reservoir A, contained 0.005 M ammonium formate dissolved in 1000 ml water, adjusted to pH 4.0 with $H_3PO_4$, and a second reservoir, Reservoir B, contained acetonitrile. The gradient was as follows: at the initial time, 40% Reservoir A and 60% Reservoir B; time 28.5 min 36% Reservoir A and 64% Reservoir B; and at time 43.0 min 36% Reservoir A and 64% Reservoir B. The system equilibrated at 7 min and a flow rate of 1.0 ml/min. The detector was set for 245 nm. The sample volume was 10 μl and the diluent was acetonitrile: water 50:50. As commonly known by the skilled artisan, the mobile phase composition and flow rate may be varied in order to achieve the required system suitability.

The sample was prepared by weighing accurately about 10 mg of Rosuvastatin Ca sample in a 20 ml amber volumetric flask. Dissolving the sample with 10 ml of acetonitrile and diluting to the desired volume with water.

Thereafter, the freshly prepared sample was injected. The sample solutions were injected into the chromatograph and the chromatogram of sample was continued up to the end of the gradient. Thereafter, the areas for each peak in each solution was determined using a suitable integrator. The calculations were obtained using the following formula:

Impurity Profile Determination $$\% \text{ impurity} = \frac{\text{area impurity in sample}}{\text{Total area}} \times 100$$

Example 1

A 250 ml flask equipped with a mechanical stirrer was charged with EtOH (100 mL) and t-Butyl-rosuvastatin (10 g). To the suspension, NaOH 1N 1.5 eq.(27.93 mL) was added portionwise at ambient temperature. The mixture was stirred at ambient temperature for one hour. After 1 hour, the resulting clear solution was filtered under reduced pressure with Synter and Hyflo to eliminate the small particles present in the solution. [HPLC sample at the end of reaction]. Then the reaction mixture was concentrated under reduced pressure at 60° C. to obtain a residue (17.79 gr) that contained the sodium salt. [HPLC sample after evaporation]. To this residue was added 100 mL water and the solutions was stirred at ambient temperature for 5 minutes. The aqueous phase was washed with EtOAc (3×100 mL). [HPLC sample of aqueous phase and sample of the organic phase]. Traces of EtOAc in the aqueous phase were distilled off under reduced pressure at 60° C. Make-up of water was done (35 mL-40 mL) at the end of the evaporation. To this solution $CaCl_2$ 1N (20 mL) was added dropwise over 10 minutes at ambient temperature resulting in precipitation of the calcium salt. The reaction mixture was then stirred at 15° C. for 2 hours, filtered and washed with 10 mL of water to get a powdery compound (8.0 g, 86%). [HPLC dry Ca-salt, BPLC ML of Ca-salt].

Example 2

A 250 ml flask equipped with a mechanical stirrer was charged with EtOH (50 mL) and t-butyl-rosuvastatin (5 g). To the suspension, NaOH 1N 1.5 eq. (13.5 mL) was added portionwise at ambient temperature. The mixture was stirred at ambient temperature for one hour. After 1 hour, the clear solution was filtered under reduced pressure with Synter and Hyflo to eliminate the small particles present in the solution. Then the reaction mixture was concentrated under reduced pressure at 60° C. to obtain a residue that contained Na-salt.

To this residue was added 50 mL water, and the solution was stirred at ambient temperature for 5 minutes. The aqueous phase was washed with methyl ethyl ketone ("MEK") (3×50 mL). Traces of MEK in the aqueous phase were distilled off under reduced pressure at 60° C. Make-up of water was done (15 mL-20 mL) at the end of the evaporation. To this solution $CaCl_2$ 1N (10 mL) was added dropwise over 10 minutes at ambient temperature to precipitate the calcium salt. The reaction mixture was then stirred at 15° C. for 2 hrs, filtered and washed with water to get s powdery compound (2.3 g, 50%).

Example 3

A 100 ml flask equipped with a mechanical stirrer was charged with EtOH (50 mL) and t-butyl-rosuvastatin (5 g). To the suspension, NaOH 1N 1.5 eq. (13.96 mL) was added portionwise at ambient temperature. The mixture was stirred at ambient temperature for one hour. After 1 hour, the clear solution was filtered under reduced pressure with Synter and Hyflo to eliminate the small particles present in the solution. Then the reaction mixture was concentrated under reduced pressure at 40° C. to obtain a residue (10.0 g) that contained Na-salt. To this residue was added 45-50 mL water and the solution was stirred at ambient temperature for 5 minutes. The aqueous phase was washed with Toluene (3×25 mL). The solution was filtered under reduced pressure with Synter and Carbon after the first extraction. Traces of toluene in the aqueous phase were distilled off under reduced pressure at 400C. Make-up of water was done (25 mL-30 mL) at the end of the evaporation. To this solution $CaCl_2$ 1N (10 mL) was added dropwise over 10 minutes at ambient temperature to precipitate rosuvastatin calcium. The reaction mixture was then stirred at ambient temperature for 2 hours, filtered and washed with 10 mL of water to get a powdery compound (3.8 g, 81.6%).

Example 4

A 100 ml flask equipped with a mechanical stirrer was charged with EtOH (50 mL) and t-butyl-rosuvastatin (5 g). To the suspension, NaOH 1N 1.5 equivalents (13.96 mL) was added portionwise at ambient temperature. The mixture was stirred at ambient temperature for one hour. After 1 hour, the clear solution was filtered under reduced pressure with Synter and Hyflo to eliminate the small particles present in the solution. Then the reaction mixture was concentrated under reduced pressure at 40° C. to obtain a residue (10.0 g) that contained Na-salt. To this residue was added 45-50 mL water and the solution was stirred at ambient temperature for 5 minutes. The aqueous phase was washed with di-ethyl carbonate ("DEC") (3×25 mL). Traces of DEC in the aqueous phase were distilled off under reduced pressure at 40° C. Make-up of water was done (25 mL-30 mL) at the end of the evaporation. To this solution, $CaCl_2$ 1N (10 mL) was added dropwise over 10 minutes at ambient temperature to precipitate rosuvastatin calcium. The reaction mixture was then stirred at ambient temperature for 2 hours, filtered and washed with 10 mL of water to get a powdery compound (4.0 g, 85.9%).

Example 5

Extraction with Methyl Tert-Butyl Ether (MTBE)

A 100 ml flask equipped with a mechanical stirrer was charged with EtOH (50 mL) and t-butyl-rosuvastatin (5 g). To the suspension NaOH 1N 1.5 eq (13.96 mL) was added portion-wise at ambient temperature. The mixture was stirred at ambient temperature for one hour. After 1 hr, the clear solution was filtered under reduced pressure with Synter and Hyflo to eliminate the small particles present in the solution. Then the reaction mixture was concentrated under reduced pressure at 40° C. to obtain a residue (10.0 g) that contained Na-salt. To this residue was added 45-50 mL water and the solution was stirred at ambient temperature for 5 min. The aqueous phase was washed with MTBE (3×25 mL). Traces of MTBE in the aqueous phase were distilled off under reduced pressure at 40° C. Make-up of water was done (25 mL-30 mL) at the end of the evaporation. To this solution, $CaCl_2$ 1N (10 mL) was added dropwise over 10 min. at ambient temperature. The reaction mixture was then stirred at ambient temperature for 2 hrs, filtered and washed with 10 mL of water to get a powdery compound (3.0 g, 64.4%).

Example 6

Extraction with Iso-Butyl Acetate

A 100 ml flask equipped with a mechanical stirrer was charged with EtOH (50 mL) and t-Butyl-Rosuvastatin (5 g). To the suspension NaOH 1N 1.5 eq (13.96 mL) was added portion-wise at ambient temperature. The mixture was stirred at ambient temperature for one hour. After 1 hr the clear solution was filtered under reduced pressure with Synter and Hyflo to eliminate the small particles present in the solution. Then the reaction mixture was concentrated under reduced pressure at 40° C. to obtain a residue (10.0 g) that contained Na-salt. To this residue was added 45-50 mL of water and the solutions was stirred at ambient temperature for 5 minutes. The aqueous phase was washed with i-Butyl Acetate (3×25 mL).

Traces of i-Butyl Acetate in the aqueous phase were distilled off under reduced pressure at 400C. Make-up of water was done (25 mL-30 mL) at the end of the evaporation. To this solution $CaCl_2$ 1N (10 mL) was added dropwise over 10 min. at ambient temperature. The reaction mixture was then stirred at ambient temperature for 2 hrs, filtered and washed with 10 mL of water to get a powdery compound (4.4 g, 94.51%).

Example 7

Preparation in $ACN/H_2O$

A 250 ml flask equipped with a mechanical stirrer was charged with ACN (25 mL), t-Butyl-Rosuvastatin (5 g), $H_2O$ (25 mL) and NaOH pellets (1.86g). The mixture was stirred at ambient temperature for 2 hours. The phases were separated in a separating ftunnel. The aqueous phase was concentrated under reduced pressure to obtain an oily residue (12.0 g). To this residue was added water (40 ml) and 5.5 g $CaCl_2$. The solution was stirred at ambient temperature for 15 hours (overnight) to form a white precipitate. The organic phase was concentrated under reduced pressure to obtain an oily residue (13.0 g). To this residue were added 40 mL water and 5.5 g $CaCl_2$. The solution was stirred at ambient temperature for 15 hours (over night) to form a white precipitate. Both parts were filtered and washed with 10 mL of water to get a powdery compound. (0.86 g from aqueous phase, 4.01 g from organic phase)

Example 8

Preparation in Toluene/$H_2O$)

A 250 ml flask equipped with a mechanical stirrer was charged with toluene (25 mL), 5 g t-Butyl-Rosuvastatin, 25 mL $H_2O$, 0.75 g of TBAB (tetrabutylammonium bromide) (15% w/w) and 1.86 g NaOH pellets. The mixture was stirred at ambient temperature for 2 hours. The phases were separated in an apparatus funnel. Traces of toluene in the aqueous phase were distilled off under reduced pressure at 40° C. to obtain a thick slurry (36.0 g). To this slurry was added 49.5 g $CaCl_2$ 1N dropwise. The solution was stirred at ambient temperature for 1.5 hours, filtered and washed with 10 mL of water to get a powdery compound.

Example 9

Preparation in Chlorobenzene (MCB)/$H_2O$

A 250 ml flask equipped with a mechanical stirrer was charged with chlorobenzene (50 mL), 5 g t-Butyl-Rosuvastatin, 50 mL $H_2O$, 0.75 g TBAB (tetrabutylammonium bromide) (15% w/w) and 1.12 g NaOH pellets. The mixture was stirred at ambient temperature for 8 hours. The phases were separated in an separating funnel. Traces of MCB in the aqueous phase were distilled off under reduced pressure at 40° C. to obtain a slurry (24.0 g). Make-up of water was done (26 mL) at the end of the evaporation to obtain a clear solution. To this solution was added 3.3 g $CaCl_2$ in 10 mL water dropwise. The solution was stirred at ambient temperature for 2 hours, filtered and washed with 10 mL of water to get a powdery compound.

Example 10

Preparation in Toluene/$H_2O$, 5 eq NaOH)

A 250 ml flask equipped with a mechanical stirrer was charged with toluene (25 mL), 5 g t-Butyl-Rosuvastatin, 25 mL $H_2O$, 0.75 g TBAB (tetrabutylammonium bromide) (15% w/w) and 1.86 g NaOH pellets. The mixture was stirred at ambient temperature for 2 hours. The phases were separated in a separation ftunnel. Traces of toluene in the aqueous phase were distilled off under reduced pressure at 40° C. to obtain a slurry (24.0 g). Make-up of water was done (26 mL) at the end of the evaporation to obtain a clear solution. To this solution was added 3.3 g $CaCl_2$ in 10 mL water dropwise. The solution was stirred at ambient temperature for 2 hours, filtered and washed with 10 mL of water to get a powdery compound.

Example 11

Using Solid NaOH and $CaCl_2$

A 250 ml flask equipped with a mechanical stirrer was charged with 50 mL EtOH, 11 lmL water and 5 g t-Butyl-Rosuvastatin then NaOH (0.44 g, 1.2 eq) was added in portions. The mixture was stirred at ambient temperature for 2 hours. The clear solution was filtered under reduced pressure with Synter and Hyflo to eliminate the small particles present in the solution. Then the reaction mixture was concentrated under reduced pressure at 50° C. to obtain a residue (10.0 g) that contained Na-salt. To this residue was added 50 mL of water and the solution was stirred at ambient temperature for 5 minutes. The aqueous phase was washed with EtOAc (3×25 mL). Traces of EtOAc in the aqueous phase were distilled off under reduced pressure at 50° C. Make-up of water was done (25 mL-30 mL) at the end of the evaporation. To this solution 1.03 g of $CaCl_2$ pellets was added. The reaction mixture was then stirred at ambient temperature for 2 hrs, filtered and washed with 1 vol. of water to get a powdery compound (4.62 g, 99.2%).

Example 12

Impurity Profile for CRESTOR

| Sample | RRT 0.54 | RRT 1 | RRT 1.26 | RRT 1.31 | RRT 1.41 | RRT 1.56 | RRT 1.71 | RRT 3.99 |
|---|---|---|---|---|---|---|---|---|
| Crestor 40 mg Lot | 0.04 | 99.45 | 0.28 | 0.01 | 0.01 | 0.01 | 0.06 | 0.14 |

Having thus described the invention with reference to particular preferred embodiments and illustrative examples, those in the art would appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications.

What is claimed is:

1. A process for producing rosuvastatin calcium comprising:
   a) reacting a $C_1$ to $C_4$ alkyl ester of rosuvastatin with a base in presence of a $C_1$ to $C_4$ alcohol to obtain a solution;
   b) concentrating the solution to obtain a residue;
   c) combining the residue with water to obtain an aqueous solution;
   d) washing the aqueous solution with a water immiscible organic solvent;
   e) removing traces of the organic solvent;
   f) adding a source of calcium to the solution to precipitate rosuvastatin calcium; and
   g) recovering the rosuvastatin calcium salt.

2. The process of claim 1, wherein the ester is a methyl ester.

3. The process of claim 1, wherein the ester is a t-butyl ester.

4. The process of claim 1, further comprising the step of stirring before step (b).

5. The process of claim 1, wherein concentrating in step (b) is carried out by evaporation.

6. The process of claim 5, wherein evaporation is carried out under reduced pressure.

7. The process of claim 1, wherein reacting is carried out by adding the base to a suspension of the ester in the alcohol.

8. The process of claim 7, wherein the alcohol is ethanol.

9. The process of claim 1, wherein the organic solvent is a $C_4$ to $C_7$ ester or ketone.

10. The process of claim 9, wherein the ester is ethylacetate.

11. The process of claim 1, wherein removing in step (e) is carried out by evaporation.

12. The process of claim 11, wherein the evaporation is carried out under reduced pressure.

13. The process of claim 1, wherein the source of calcium is calcium chloride.

14. The process of claim 1, wherein the recovering step is carried out with filtration.

15. The process of claim 1, wherein the base is selected from the group consisting of sodium, potassium and barium hydroxide.

16. A process for producing rosuvastatin calcium salt comprising:
   a) combining a suspension of t-butyl ester of rosuvastatin in ethanol with sodium hydroxide to obtain a solution, and stirring during or after the combining;
   b) evaporating the solution under reduced pressure to obtain a residue;
   c) combining the residue with water to obtain an aqueous solution;
   d) washing the aqueous solution with ethyl acetate;
   e) evaporating traces of the ethyl acetate under reduced pressure;
   f) adding calcium chloride to the solution to precipitate rosuvastatin calcium; and
   g) filtering the rosuvastatin calcium salt.

17. A process for producing rosuvastatin calcium salt comprising:
   a) reacting a $C_1$ to $C_4$ alkyl ester of rosuvastatin in a water immiscible phase, with a base in an aqueous phase, in presence of a phase transfer catalyst to obtain rosuvastatin in the aqueous phase;
   b) adding a source of calcium to the aqueous phase to precipitate rosuvastatin calcium; and
   c) recovering the rosuvastatin calcium salt; with the proviso that:
      (i) the process further comprising a step of removing traces of the water immiscible solvent before adding a source of calcium; wherein the ester is a t-butyl ester:
      (ii) the process further comprises stirring during the reaction;
      (iii) wherein the water immiscible phase is a solvent selected from the group consisting of substituted and unsubstituted C5 to C12 hydrocarbon, C4 to C7 ester, C4 to C7 ketone and mixtures thereof; or
      (iv) the hydrocarbon is toluene or chlorobenzene.

18. The process of claim 17, further comprising a step of removing traces of the water immiscible solvent before adding a source of calcium.

19. The process of claim 17, wherein the ester is a t-butyl ester.

20. The process of claim 17, further comprising stirring during the reaction.

21. The process of claim 17, wherein the water immiscible phase is a solvent selected from the group consisting of substituted and unsubstituted $C_5$ to $C_{12}$ hydrocarbon, $C_4$ to $C_7$ ester, $C_4$ to $C_7$ ketone and mixtures thereof.

22. The process of claim 21, wherein the hydrocarbon is toluene or chlorobenzene.

23. The process of claim 17, wherein the phase transfer catalyst is an alkyl, aryl, alkaryl or arylalkyl ammonium salt.

24. A process for producing rosuvastatin calcium salt comprising:
   a) reacting, t-butyl ester of rosuvastatin with sodium hydroxide in presence of water, a tetrabutylammonium phase transfer catalyst and an organic solvent selected from the group consisting of toluene and chlorobenzene to obtain rosuvastatin in the water;
   b) removing traces of the toluene or chlorobenzene from the water;
   c) adding calcium chloride to the water to precipitate rosuvastatin calcium; and
   d) filtering the rosuvastatin calcium salt.

25. The process of claim 24, further comprising stirring during the reaction.

26. A process for producing rosuvastatin calcium salt substantially free of impurities comprising the steps of:
   a) reacting a $C_1$ to $C_4$ ester of rosuvastatin with a base in a two phase system of water and acetonitrile;
   b) concentrating the water phase to obtain a residue;
   c) adding a source of calcium and water to the residue to form a solution in water; and
   d) recovering rosuvastatin calcium as a precipitate.

27. The process of claim 26, further comprising stirring during the reaction.

28. The process of claim 1, 16, 17, 24, or 26, wherein the calcium salt contains less than or of about 0.4% total impurities as measured by area percentage HPLC.

29. The process of claim 28, wherein the impurities is of or less than about 0.3% as measured by area percentage HPLC.

30. The process of claim 1, 16, 17, 24, or 26, wherein the calcium salt does not have detectable level of impurities when measured by HPLC at RRT 0.62, 1.18, 1.26, 1.60, 2.68, 3.66, 3.89, 3.93 and 4.10.

31. The process of claim 30, wherein the impurities are less than about 0.01% as measured by HPLC area percentage.

32. A process for producing rosuvastatin calcium comprising:
   a) preparing a solution of rosuvastatin sodium;
   b) concentrating the solution to obtain a residue;
   c) combining the residue with water to obtain an aqueous solution;
   d) washing the aqueous solution with a water immiscible organic solvent;
   e) removing traces of the organic solvent;
   f) adding a source of calcium to the solution to precipitate rosuvastatin calcium; and
   g) recovering the rosuvastatin calcium salt.

33. Rosuvastatin calcium in solid state having less than or of about 0.4% total impurities as measured by area percentage HPLC.

34. The rosuvastatin calcium of claim 33, wherein the impurities is of or less than about 0.3% as measured by area percentage HPLC.

35. Rosuvastatin calcium in solid state, wherein the calcium salt does not have detectable level of impurities when measured by HPLC at RRT 1.26.

36. The rosuvastatin calcium of claim 35, wherein the calcium salt does not have further detectable level of impurities when measured by HPLC at RRT 0.62, 1.18, 1.60, 2.68, 3.66, 3.89, 3.93 and 4.10.

37. The rosuvastatin calcium of claim 36, wherein the impurities are less than about 0.01% as measured by HPLC area percentage.

38. The process of claim 1, 16, 17, 24, or 26, wherein the process is performed in one-pot.

* * * * *